United States Patent [19]

Josse et al.

[11] 4,187,322

[45] Feb. 5, 1980

[54] POWDER COMPOSITIONS CONTAINING VITAMIN C ACTIVE COMPONENT

[75] Inventors: René Josse, Rixheim, France; Heinrich Kläui, Riehen, Switzerland

[73] Assignee: Hoffmann-La Roche Inc., Nutley, N.J.

[21] Appl. No.: 739,879

[22] Filed: Nov. 8, 1976

[30] Foreign Application Priority Data

Nov. 30, 1975 [CH] Switzerland ................. 15466/75

[51] Int. Cl.² .............................................. A23K 1/00
[52] U.S. Cl. ..................................... 426/72; 426/311; 426/623; 252/403
[58] Field of Search ................. 426/309, 310, 72, 311, 426/541, 73, 543, 545, 623, 622, 630, 640, 635, 546, 459–460, 462, 461, 466, 463, 468, 305, 507; 424/280; 252/403

[56] References Cited

U.S. PATENT DOCUMENTS

| 2,775,521 | 12/1956 | Mateles et al. | 426/311 X |
| 3,247,065 | 4/1966 | Koff | 424/280 |
| 3,767,824 | 10/1973 | Keyser et al. | 426/73 X |

OTHER PUBLICATIONS

Morrison "Feeds and Feeding" Morrison Publishing Co., 1957, pp. 144–145.

Primary Examiner—R. B. Penland
Attorney, Agent, or Firm—Jon S. Saxe; Bernard S. Leon; William M. Farley

[57] ABSTRACT

Stable, dry, free-flowing powder compositions containing ascorbic acid or salts thereof, methods for their preparation and feedstuff containing the powder compositions are disclosed.

17 Claims, No Drawings

POWDER COMPOSITIONS CONTAINING VITAMIN C ACTIVE COMPONENT

BACKGROUND OF THE INVENTION

The utilization of ascorbic acid and certain salts thereof as a feed additive is well-known. However, since these materials are relatively unstable, either alone or in combination with other water-soluble vitamins, there are many problems associated with the stability of a vitamin C active component in animal feedstuffs. Certain conditions found in a feedstuff environment, e.g. atmospheric oxygen, moisture, enzymes, certain chemicals as, for example, certain iron salts as well as the mechanical and physical stresses encountered in the manufacture and processing of the animal feedstuffs, (e.g., during pelletizing) contribute to the degradation of the vitamin C active component therein.

There have been numerous efforts in the prior art to prepare stable forms of the vitamin C active component in dry, particulate compositions for supplementation of animal feedstuffs.

The major procedures described in the art involve the coating of the vitamin C active component with such substances as ethyl cellulose, cetyl alcohol, mixtures of paraffin wax and low molecular weight polyethylene and the like. The vitamin materials are usually prepared by mixing particles of a vitamin C active component with a solvent containing the coating material and, subsequently, removing the solvent. However, these coated vitamin C active materials have been found to be unsatisfactory. First of all, the particles which result are usually much larger than the particles of the uncoated starting material. In addition, these coated particles often agglomerate leading to such deleterious properties as a lack of uniformity in the feed and a loss of good flow properties. Thus, such materials are unsuitable for admixtures in feedstuffs.

Another method used to overcome the problem of stability is the addition of large excesses of the vitamin C active component (i.e., up to 200% excess) to a feedstuff during the manufacturing process.

It is an object of this invention, therefore, to provide novel, dry, free-flowing compositions containing a vitamin C active component which will be suitable for admixture with, and stable in, aminal feedstuffs.

DETAILED DESCRIPTION OF THE INVENTION

This invention relates, in general, to novel compositions and to a process for preparing them. More particularly, this invention relates to compositions containing a vitamin C active component which is stabilized against deterioration of the vitamin C active component in animal feedstuffs, to a process for preparing such compositions and to the fortified feedstuffs resulting therefrom.

By the process of this invention, dry, free-flowing powder compositions comprising a cereal grain and from about 15% to about 45% by weight, based on the weight of the powder composition, of a vitamin C active component are prepared wherein the vitamin C active component in the powder composition is stabilized against degradation in feedstuffs.

As used herein, the term "a vitamin C active component" is a substance selected from the group consisting of ascorbic acid and salts of ascorbic acid with bases acceptable in animal feeds. When a salt is used, inorganic salts, such as alkali metal and alkaline earth metal salts are preferred. Especially preferred are sodium ascorbate and potassium ascorbate.

Ascorbic acid (vitamin C) is characterized as being soluble in water but not in oil, being a strong acid in solution and a strong reducing agent which can be easily oxidized. Where oxidized, however, ascorbic acid loses its therapeutic value.

In addition to the vitamin C active component, i.e., ascorbic acid and certain salts thereof, the compositions of this invention can also contain other water-soluble vitamins or derivatives thereof as, for example, the B-complex vitamins—biotin, choline, choline chloride, folic acid, niacine and the like, pantothenic acid, calcium pantothenate, thiamine, raboflavin and the like.

The term "cereal" refers to those products which are the edible seeds of the grass family (Gramineae), e.g., wheat, rye, oats, rice, maize, barley and the like. As used herein, the term "cereal grain" refers to ground cereal products (e.g., maize grain, wheat grain and the like) having a particle size range of from about 0.25 mm to about 4 mm and, preferably, from about 0.25 mm to about 3 mm. Especially preferred for the purposes of this invention are ground cereal products which have a particle size range of from about 0.25 mm to about 2 mm.

The cereal grain used in the process and composition of this invention is pre-swollen prior to its use. Pre-swelling, a procedure known in the art, is accomplished by mixing the cereal grain with water and heating the resulting mixture in an autoclave to a temperature of from about 100° C. to about 140° C., preferably at about 120° C., for from about 3 minutes to about 8 minutes, preferably for about 5 minutes. The mixture is then removed from the autoclave and dried in an oven at a temperature ranging from about 60° C. to about 100° C., preferably about 80° C. Drying is continued until there is a water loss from the mixture of from about 10% to about 30% by weight, based on the total weight of the mixture. The preferred weight loss is about 20% by weight. Drying time should be kept as short as possible, preferably about one hour.

The resulting pre-swollen cereal grain does not agglutinate in the aqueous mixture.

In addition, this pre-swelling operation serves to destroy any enzymes which may be present in the cereal grain.

The pre-swollen aqueous cereal grain mixture, prepared as described above, is then mixed with an aqueous solution of the vitamin C active component, e.g., ascorbic acid or a salt thereof.

The vitamin C active component in the aqueous solution is absorbed by the pre-swollen cereal grain.

Both the preparation of the aqueous solution of the vitamin C active component and the mixing of this aqueous solution with the pre-swollen cereal grain are achieved by any simple mixing procedure under an inert gas atmosphere, i.e., nitrogen.

Drying of the resulting product is also carried out in the presence of an inert gas atmosphere at temperatures of from about 50° C. to about 80° C. and, preferably, at a temperature of about 60° C. The total drying time is about 6–8 hours. The drying process can be interrupted, after 2–3 hours, to break up any coarse lumps which may develop and, thus, shorten the drying process.

Drying over this temperature range can be at atmospheric pressure or pressures below atmospheric can be employed.

In the alternative, drying can be carried out at room temperature in a cold air stream. This process is considerably longer, e.g., from about 36 to 48 hours.

After drying the resulting product can be comminuted by known procedures, e.g., trituration, air milling and the like. The final product should have a particle size range of from about 250 microns ($\mu$) to about 2000 microns ($\mu$) to be suitable for admixture with animal feedstuffs.

The cereal grain mixture, prior to the pre-swelling procedure contains from about 40% to about 70% by weight of the cereal grain with from about 60% to about 30% by weight of water. All weight percentages are based on the total weight of the resulting cereal grain mixture.

The concentration of the vitamin C active component in the aqueous solution to be mixed with the pre-swollen cereal grains should be as high as can be achieved depending on the water solubility of the particular vitamin C active component. For example, ascorbic acid concentrations can range from about 25% to 35% on a weight/volume basis. Preferably, the concentration should be about 30% (wt./vol.). Sodium ascorbate concentrations can range from about 40% to about 70% on a weight/volume basis. The preferable concentration is about 60% (wt./vol.).

Solutions of other water-soluble vitamins can also be prepared with their concentrations in aqueous solutions again dependent on their water solubilities.

The final vitamin content of the powder composition of this invention depends on the concentration of the vitamin C active component in the aqueous solution used. The vitamin C active component content in the powder composition is at least about 10% by weight based on the weight of the powder composition.

Where ascorbic acid is the vitamin C active component, its concentration in the powder compositions ranges from about 15% by weight to about 25% by weight. The preferred concentration of ascorbic acid in the powder composition is about 18% by weight.

When sodium ascorbate is the vitamin C active component, its concentration in the powder compositions ranges from about 25% by weight to about 45% by weight. The preferred concentration of sodium ascorbate in the powder compositions is from about 30% by weight to about 40% by weight with an especially preferred concentration range of from about 35% by weight to about 38% by weight.

The powder compositions of this invention have utility in the vitamin fortification of animal feedstuffs, especially with a vitamin C active component. By the term "feedstuffs" is meant animal food and food supplements and, more particularly, feeds and feed supplements for livestock, poultry and the like. The term includes feeds which are fortified with one or more supplemental materials contained in pellets or other common shapes.

It is usual practice to fortify such animal feeds with other nutritional materials including vitamins. However, as noted earlier, vitamins, including vitamin C, are readily susceptible to, for example, oxidative, heat or pressure deterioration in admixture with, or processing of, such feedstuffs.

For instance, in the fortification of ground and mixed feeds for livestock, poultry, etc., it would be highly desirable to have a stable, dry, free-flowing vitamin active composition which could be readily and uniformly admixed with such feeds, which could withstand subsequent manufacturing procedures and which would remain stable over relatively long storage periods.

Examples of the manufacturing procedures which fortified animal feedstuffs may undergo including press granulation, wherein the feedstuff is added to a pelletizing mill with steam and then pressurized through a die, and extrusion, wherein the feedstuff is extruded under pressure and often under heat through various shaped dies.

The powder compositions of this invention, containing a vitamin C active component, are characterized as having a particle size range and being dry and free-flowing so as to be suitable for facile and uniform admixture with the various animal feeds. These powder compositions are further characterized as having superior stability, not only against any moisture, enzymes and chemical salts present in a particular feedstuff but also against the pressure and heat which may be encountered in the subsequent processing of the fortified feed, as compared to either vitamin C active components alone or prior art vitamin C compositions.

When used to fortify animal feedstuff, the powder compositions of this invention should be present in such a concentration as to provide from about 100 milligrams to about 200 milligrams of the vitamin A active component per kilogram of the animal feedstuff.

The following Examples illustrate the invention.

EXAMPLE 1

100 grams of maize grain and 80 ml. of distilled water were admixed for 3–5 minutes at room temperature. The mixture was then placed in an autoclave heated to 120° C. and maintained at that temperature for 5 minutes. The resulting product was removed from the autoclave to an oven and dried at 80° C. for approximately 60 minutes or until the moisture loss was about 20%.

60 grams of sodium ascorbate were dissolved under a nitrogen atmosphere, in 100 ml. of distilled water at 70° C.

This solution (60% wt./vol.) was then added to the pre-swollen maize grain. The resulting mixture was stirred for 15 minutes and then dried, under a nitrogen atmosphere, at 60° C. and reduced pressure, e.g., 150 mm. Hg. After drying for 2–3 hours, the granules were removed from the oven, ground in a mortar to remove any lumps, and then dried to constant weight (total drying time—about 6 to 8 hours).

The dried product was comminuted and the resulting powder composition was screened to separate the particles in the range of from about 250$\mu$ to about 2000$\mu$.

EXAMPLE 2

To determine the sodium ascorbate content of powder compositions prepared as described in Example 1, one gram of each powder composition was ground in a mortar to a fine powder.

An extraction solution was prepared by mixing 1000 ml. of methanol, 20 ml. of a 0.1% (wt./vol.) aqueous oxalic acid solution and 200 ml. of benzine (boiling range 40°–60° C.).

The finely ground powder compositions were extracted with 250 ml. of this extraction solution. 50 ml. of each extract were pipetted into a test tube containing 25 ml. of a 0.1% (wt./vol.) aqueous oxalic acid solution and shaken vigorously. After standing, the volume of the organic phase was measured. 2 ml. of the organic phase were removed and the sodium ascorbate content was determined, i.e., by titration with a $10^{-3}$ molar solution of the sodium salt of 2,6-dichlorophenolindophenol which had been previously standardized against a sodium ascorbate solution of known concentration.

From this titration data and the total volume of the organic phases, the sodium ascorbate contents of the powder compositions prepared as in Example 1 were determined to be about 36% to about 38% by weight.

EXAMPLE 3 gracz in Zeitschrift fur analytische Chemie, 253, 271-274(1971).

The data are listed in Table 1. The percent ascorbic acid or sodium ascorbate content reported after 2 and 4 month storage periods was based on the content of the vitamin C active component in the feed after pelletizing.

The data demonstrate the superior stability of a vitamin C active component when used in the powder concentrations of this invention.

Table I

| | | | | Stability of Vitamin C Component in Feeds | | | |
|---|---|---|---|---|---|---|---|
| | | Vitamin C | Vitamin C | Vitamin C Active Component Content | | | |
| | Vitamin C | component, | component | % Content After 2 Months Storage | | % Content After 4 Months Storage | |
| Feed | component | Theoretical | After Pelletizing, % | @ Room Temp. | @ 45° C. | @ Room Temp. | @ 45° C. |
| A | Ascorbic Acid | 200 mg/kg | 65 | 70 | 75 | 77 | 41 |
| B | Sodium Ascorbate | 200 mg/kg | 59 | 30 | 17 | <8.5 | <8.5 |
| C | Sodium Ascorbate Composition from Example 1 | 200 mg/kg | 100 | 100 | 100 | 90 | 80 |
| D | Ascorbic acid Composition from Example 3 | 200 mg/kg | 93 | 88 | 88 | 93 | 63 |

22 grams of ascorbic acid were dissolved, under a nitrogen atmosphere, in 100 ml. of distilled water at 70° C. This solution (22% wt./vol.) was then added to 100 grams of maize grain which had been pre-swollen as described in Example 1.

The resulting mixture was stirred for 15 minutes and then dried, under a nitrogen atmosphere, at 60° C. and a pressure of 150 mm. Hg. After 2 to 3 hours, the material was removed from the oven, ground in a mortar and then dried to constant weight. After grinding the dried powder composition to a fine powder, the particles in the particle size range of $250\mu$–$2000\mu$ were separated by screening.

The ascorbic acid content, determined as described in Example 2, was 18% by weight.

EXAMPLE 4

This example illustrates the stability of sodium ascorbate when present in the powder compositions prepared as described in Examples 1 and 3 above.

Feed premixes fortified with ascorbic acid or sodium ascorbate were prepared by admixing one kilogram portions of an animal feed premix with the following:

| Feed | Vitamin C Component |
|---|---|
| A | 200 mg. ascorbic acid |
| B | 200 mg. sodium ascorbate |
| C | 533 mg. of Composition from Example 1 |
| D | 909 mg. of Composition from Example 3 |

Each fortified feed was pelletized by press granluation in which each mixture is added to a pelletizing mill, admixed with steam and then forced by pressure through dies to form the pellets.

The stability of the vitamin C component in each feed was determined by mixing 10 grams of the pelletized feed, after grinding to a fine powder, with 100 ml. of 0.2% (wt./vol.) aqueous succinic acid. This mixture was shaken for 3 minutes and then filtered.

10 ml. of filtrate were removed and its pH was adjusted to 3.5 using 20 ml. of 0.2% aqueous succinic acid in a buffer solution. The quantity of ascorbic acid or sodium ascorbate in this solution was determined by potentiometric titration with 2,6-dichlorophenol-indophenol following the procedure described by G. Pon-

We claim:

1. A dry, stable, free-flowing powder composition which comprises pre-swollen cereal grain having absorbed therein from about 15% to about 45% by weight, based on the total weight of the powder composition, of a vitamin C active component selected from the group consisting of ascorbic acid, an alkali metal salt thereof and an alkaline earth metal salt thereof and wherein said vitamin C active component is obtained from an aqueous solution of said acid or said salts.

2. The powder composition of claim 1 which comprises from about 15% to about 25% by weight of ascorbic acid as the vitamin C active component.

3. The powder composition of claim 2 which comprises about 18% by weight of ascorbic acid as the vitamin C active component.

4. The powder composition of claim 1 which comprises from about 25% to about 45% by weight of sodium ascorbate as the vitamin C active component.

5. The powder composition of claim 4 which comprises from about 30% to about 40% by weight of sodium ascorbate as the vitamin C active component.

6. The powder composition of claim 5 which comprises from about 35% to about 38% by weight of sodium ascorbate as the vitamin C active component.

7. The powder composition of claim 1 having a particle size range of from about $250\mu$ to about $2000\mu$.

8. A method for preparing a dry, stable, free-flowing powder composition containing a vitamin C active component which comprises (a) preparing an aqueous mixture of a cereal grain;
 (b) processing the aqueous mixture of step (a) to form a pre-swollen, non-agglutinating cereal grain in the aqueous mixture;
 (c) admixing, under an inert atmosphere, the aqueous pre-swollen, non-agglutinating cereal grain mixture of step (b) with a saturated aqueous solution of a vitamin C active component;
 (d) drying the resulting admixture in an inert gas atmosphere to prepare the dry, stable, free-flowing powder composition.

9. The method of claim 8 wherein the dried mixture of step (d) is comminuted to a particle size range of from about $250\mu$ to about $2000\mu$.

10. The method of claim 8 wherein the aqueous mixture of pre-swollen, non-agglutinating cereal grain of step (b) is prepared by
   (i) preparing an admixture of from about 40% to about 70% by weight of cereal grain with from about 60% by weight to about 30% by weight of water, all percents by weight based on the weight of the resulting admixture;
   (ii) heating the mixture of step (i) in an autoclave for from about 3 minutes to about 8 minutes at a temperature of from about 100° to about 140° C.;
   (iii) removing the mixture from the autoclave; and
   (iv) drying the mixture in an oven at a temperature of from about 60° C. to about 100° C. until there is a water loss of from about 10% to about 30% by weight based on the total weight of the initial admixture.

to thus form the aqueous mixture of pre-swollen, non-agglutinating cereal grain.

11. The method of claim 8 wherein the aqueous solution of step (c) comprises from about 25% to about 35% on a weight/volume basis of ascorbic acid as the vitamin C active component.

12. The method of claim 8 wherein the aqueous solution of step (c) comprises from about 40% to about 70% on a weight/volume basis of sodium ascorbate as the vitamin C active component.

13. The method of claim 8 wherein the drying procedure of step (d) is carried out at a temperature of from about 50° C. to about 80° C.

14. A stable, vitamin C fortified animal feedstuff which comprises an admixture of (a) an animal feedstuff and (b) a dry, stable, free-flowing powder composition which comprises pre-swollen cereal grain having absorbed therein from about 15% to about 45% by weight, based on the total weight of the powder composition, of a vitamin C active component selected from the group consisting of ascorbic acid, an alkali metal salt thereof and an alkaline earth metal salt thereof and wherein said vitamin C active component is obtained from an aqueous solution of said acid or said salts.

15. The stable, vitamin C fortified animal feedstuff of claim 14 wherein the vitamin C active component of the powder composition is present in a concentration range of from about 100 milligrams to about 200 milligrams of the component per kilogram of the animal feedstuff.

16. The stable, vitamin C fortified animal feedstuff of claim 15 wherein the vitamin C active component is ascorbic acid.

17. The stable, vitamin C fortified animal feedstuff of claim 15 wherein the vitamin C active component is sodium ascorbate.

* * * * *